United States Patent [19]

Tittel

[11] Patent Number: 4,868,397

[45] Date of Patent: Sep. 19, 1989

[54] STERILIZING APPARATUS FOR OPHTHALMOLOGICAL DEVICES

[76] Inventor: Paul G. Tittel, 3203 Dry Branch Rd., White Hall, Md. 21161

[21] Appl. No.: 106,456

[22] Filed: Oct. 9, 1987

[51] Int. Cl.$^4$ ............................................. G01N 23/00
[52] U.S. Cl. .................................. 250/455.1; 422/24; 422/300
[58] Field of Search ................. 250/455.1; 422/1, 24, 422/300; 128/652

[56] References Cited

U.S. PATENT DOCUMENTS

| | | | |
|---|---|---|---|
| 3,852,032 | 12/1974 | Urbach | 422/24 |
| 4,063,890 | 12/1977 | Baron | 422/24 |
| 4,448,750 | 5/1984 | Fuesting | 422/300 |
| 4,735,209 | 4/1988 | Foody | 128/652 |
| 4,772,795 | 9/1988 | Sakurai | 250/455.1 |

*Primary Examiner*—Bruce C. Anderson
*Attorney, Agent, or Firm*—Leonard Bloom

[57] ABSTRACT

An apparatus provides for the sterilizing of bacterial and virus contracted ophthalmological devices having a portion thereof intended to contact the eye by the use of ultraviolet light. The apparatus features an enclosed light-tight housing into which are at least partially disposed ophthalmological insert sleeves. An ultraviolet light source is positioned within the housing for providing the sterilizing ultraviolet light. Each sleeve is adapted to receive removably and snugly a particular ophthalmological device to be sterilized, with a relatively tight interfit therebetween. Each sleeve is further removably and snugly received in a respective insertion aperture of the housing with a relatively tight interfit therebetween, so that the portion of the device intended to contact the eye is held by a respective sleeve in relatively close proximity to the light source. Particular specialized insertion sleeves are provided for pneumo-probes, tonometer probes and contact lenses.

23 Claims, 4 Drawing Sheets

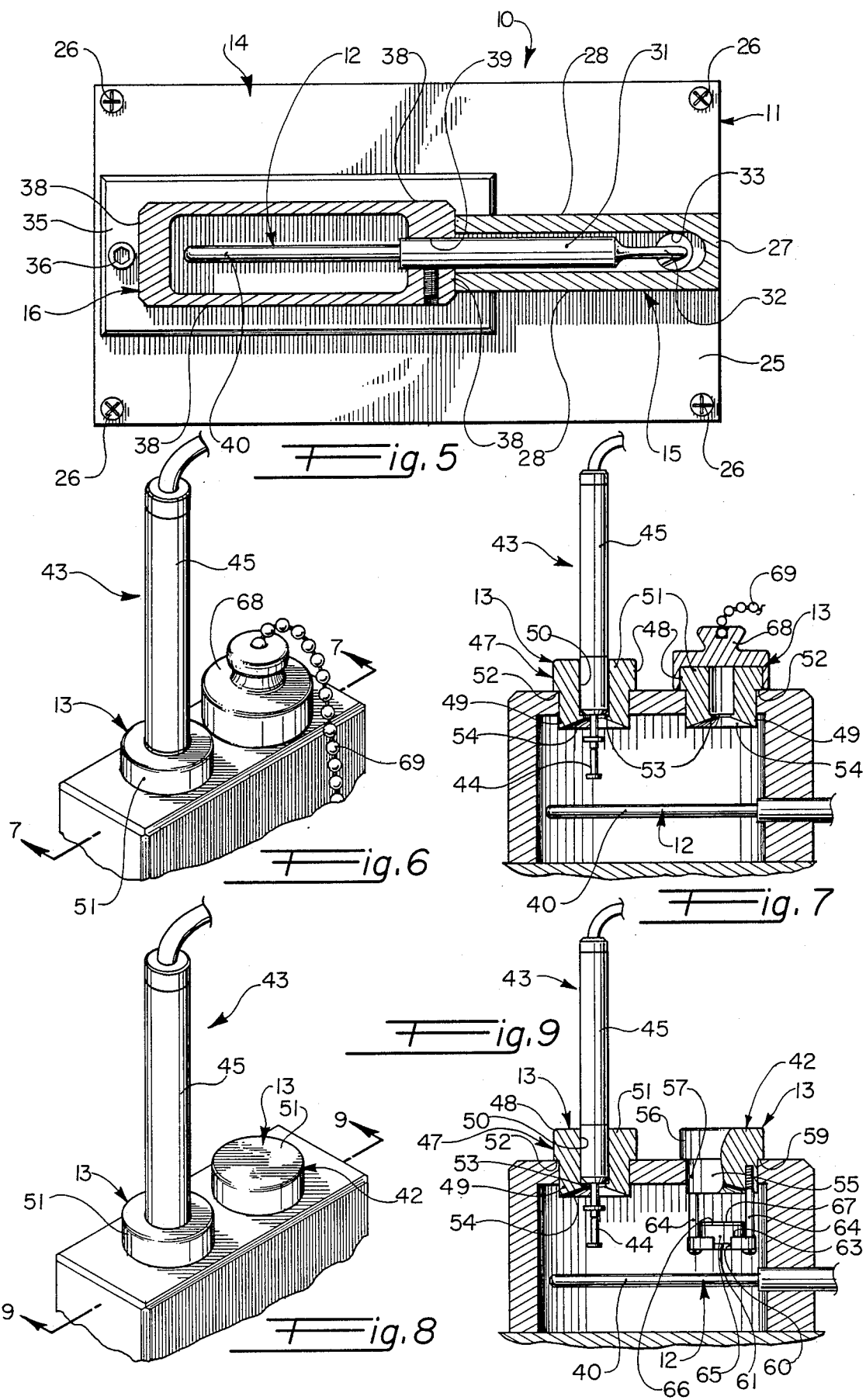

STERILIZING APPARATUS FOR OPHTHALMOLOGICAL DEVICES

FIELD OF THE INVENTION

The present invention relates to an apparatus for sterilizing ophthalmological devices, and, in particular, an apparatus for sterilizing ophthalmological probes used in eye examinations and contact lenses, wherein the device has a portion intended to be placed into contact with an eye.

BACKGROUND OF THE INVENTION

The utilization of UV light for the sterilization of air and water is well known. It is also well known to sterilize articles such as toiletries, toothbrushes, barber equipment, wearing apparel, and medical equipment, by exposure to UV light. Patents, of which I am aware, that relates to such use are as follows:

| Inventor(s) | U.S. Pat. No. | Year of Issue |
| --- | --- | --- |
| Coleman | 3,790,801 | 1974 |
| Abernathy | 3,820,251 | 1974 |
| Callahan | 3,906,236 | 1975 |
| Andary et al | 3,954,407 | 1976 |
| Blaisdell et al | 4,100,415 | 1978 |
| Tenney et al | 4,309,388 | 1982 |
| Hogan | 4,433,244 | 1984 |
| Murdock III | 4,625,119 | 1986. |

The desirability of utilizing UV light for sterilizing ophthalmological supplies and equipment has been long recognized. However, due to the susceptability of the eye to infection from a virus, bacteria or otherwise, extreme reliability is required to insure total exposure of the ophthalmological article to the sterilizing light. Unfortunately, this has severely limited the use of such apparatuses for sterilizing ophthalmological equipment and supplies. To the best of my knowledge, there is no apparatus provided which is capable of safely and reliably sterilizing ophthalmological probes, contact lenses and other devices that contact the eye during use.

In order to be reliable, such a sterilizing apparatus must precisely position the UV light relative to the article being sterilized, so that the article is exposed to UV light from essentially all angles to avoid any shadowed or shaded areas.

In order to be safe, the device must substantially prevent the leakage of light to the exterior. This is because UV light can be quite harmful to persons in the vicinity who may be exposed thereto. Also, the device must be relatively simple to use, capable of being operated by a relatively untrained individual.

Thus, it can be seen that there remains a need for an apparatus which, by the use of UV light can safely and reliably sterilize ophthalmological devices and instruments, such as test probes and contact lenses, which have a portion intended to be placed in contact with the eye. There is a further need for such an apparatus which is portable, inexpensive and is readily and safely operable by relatively untrained personnel.

SUMMARY OF THE INVENTION

Accordingly, it is the primary object of the present invention to provide an apparatus which safely and reliably sterilizes ophthalmological devices, such as test probes and contact lenses by use of UV light.

It is a further object of the present invention to provide such an apparatus that is inexpensive, portable, and is readily and safely operable by relatively untrained personnel, so that it may be used by an individual in their home to sterilize, for example, their own contact lenses.

In accordance with the teachings of the present invention, there is disclosed an apparatus for sterilizing ophthalmological instruments. This apparatus includes an enclosed housing having at least one insert sleeve aperture formed therein. An ultraviolet light source is positioned within the housing. At least one ophthalmological instrument insert sleeve is provided. Each sleeve is adapted to removably and snugly receive therein an ophthalmological instrument. Each of said sleeves is also removably and snugly received in a respective insertion aperture during use. In this fashion, each of said instruments is held by a respective sleeve in close proximity to the light source. Furthermore, light is prevented from passing between the instrument and the respective sleeve in which it is received, as well as the sleeve and the respective aperture in which it is received.

In further accordance with the teachings of the present invention, there is disclosed an apparatus for sterilizing ophthalmological instruments. This apparatus includes an enclosed insert holder. Said holder includes a housing having a highly polished reflecting interior surface. Said housing further has at least two insert sleeve apertures formed therein. An ultraviolet light source is positioned within the housing. At least two ophthalmological instrument insert sleeves are provided. Each of said sleeves is adapted having a close tolerance with a respective ophthalmological instrument, so as to selectively, removably and snugly receive therein the respective ophthalmological instrument. In this fashion, during use, light is prevented from passing between the sleeve and the respective instrument received therein. Each of said sleeves is further adapted having a close tolerance with a respective insertion sleeve aperture, so as to be selectively, removably and snugly received in the insert sleeve aperture. In this fashion, during use, light is prevented from passing between the sleeve and the respective insert sleeve aperture in which the sleeve is received. Also, during use each of said instruments is held by a respective sleeve in close proximity to the light source.

Preferably, the apparatus further includes at least one cap. Each of said caps is sized to be received over a respective sleeve, whereby light is prevented from passing through the sleeve.

In a preferred embodiment, the light source includes a transformer. A first electrical conduit means is positioned between and in electrical communication with the transformer and an external electrical power source. In this manner, electrical power from the external electrical power source is carried to the transformer. An on/off switch means is provided for selectively, manually controlling the flow of electrical power between the power source and the transformer. An electrical outlet is provided for an ultraviolet light. A second electrical conduit means is positioned between, and in electrical communication with, the transformer and the electrical outlet. In this fashion, electrical power is carried from the transformer to the outlet. Also, an ultraviolet light bulb is received in the electrical outlet, such that electrical power in the outlet energizes the bulb. Preferably, the transformer, the on/off switch and the second electrical conduit means are positioned in a transformer housing. Further, the electrical outlet is disposed through the housing of the insert holder. Also, an adjustable on/off timer switch means may be provided for manually presetting the desired time of sterilization by the ultraviolet light source.

In another preferred embodiment, the housing of the insert holder includes an upper wall and four downwardly-extending sidewalls. The upper wall has the insert sleeve apertures formed therein. Also, the light source is mounted on one of the sidewalls, such that during use the sleeves are received in a respective aperture positioned directly over the light source and in close proximity thereto.

In still another preferred embodiment, the ultraviolet light source is an ultraviolet light having a wavelength of 254 NM.

In yet another preferred embodiment, each insert sleeve aperture may accommodate various different insert sleeves adapted to accommodate various ophthalmological instruments, including contact lenses and test probes such as pneumoprobes and tonometer probes.

In one aspect of the present invention, there is disclosed an insert sleeve adapted to receive the pneumoprobe or tonometer probe having a probe body and a probe tip. This sleeve includes an insert sleeve body portion having an upper end, and a lower end. The insert sleeve body further has a longitudinal bore formed therethrough, wherein the pneumoprobe or tonometer probe to be sterilized is received in the sleeve. A boss is formed on the upper end of the sleeve body. In this fashion, an external annular shoulder is defined between the boss and the sleeve body. Further, when the sleeve is received in a respective insert sleeve aperture during use, the annular shoulder abuts the insert holder housing, thereby preventing further movement of the sleeve into the insert holder housing. An internal annular lip is formed in the bore on the lower end of the sleeve body. In this fashion, the probe is received in the insert sleeve during use. The probe body abuts the internal annular lip, thereby preventing further movement of the pneumoprobe or tonometer probe and others into the insert sleeve. The lower end of the sleeve body has a countersunk portion formed therein. The countersunk portion terminates coincident with the internal annular lip. When the probe is received in the respective sleeve during use, the probe tip thereof emerges from the lower end of the sleeve, so that the probe tip is exposed to the ultraviolet light in close proximity thereto.

In another aspect of the present invention, there is disclosed an insert sleeve adapted to receive contact lenses. This sleeve includes an insert sleeve body portion having an upper end and a lower end. A boss is formed on the upper end of the sleeve body, wherein an external annular shoulder is defined between the boss and the sleeve body. When the sleeve is received in a respective insert sleeve aperture during use, the annular shoulder abuts the insert holder housing, thereby preventing further movement of the sleeve into the insert holder housing. A pocket is suspended from and carried by the lower end of the sleeve. The pocket includes a lower shelf having an aperture formed therein. An upwardly extending annular lip is formed on the lower shelf. A clear cup member is provided. This cup member includes a bottom wall having a perimeter. The cup member further includes an upwardly-extending annular lip formed about the perimeter of the bottom wall.

The cup member is adapted to receive therein contact lenses to be sterilized. If desired, the cup may be filled with a suitable liquid media, one which does not disturb the permeability of the lens. The cup member is further adapted to be removably received in the pocket with the bottom wall of the cup member and the aperture of the lower shelf of the pocket substantially aligned with one another. In this fashion, the contact lenses are exposed to the ultraviolet light. Preferably, each insert sleeve adapted to receive contact lenses further includes a lid member adapted to be removably received on the upwardly-extending annular lip of the cup member, whereby the contact lenses are removably retained within the cup member. It is also preferred that each insert sleeve adapted to receive contact lenses further includes at least one post member having an upper end being piloted in the lower end of the insert sleeve. Each post member further has a lower end being piloted in the upwardly extending annular lip of the pocket, whereby the pocket is suspended from and carried by the lower end of the sleeve.

BRIEF DESCRIPTION OF THE DRAWINGS

FIG. 3 is a rear perspective view of the housing of the apparatus of the present invention, wherein a cap is placed on one of the sleeves.

FIG. 4 is a section view, to an enlarged scale, taken along line 4—4 of FIG. 1.

FIG. 5 is an overhead section view, taken along line 5—5 of FIG. 4.

FIG. 6 is a front perspective view of the housing of the apparatus of the present invention illustrating a probe disposed in a sleeve adapted therefor and a cap disposed on an unused sleeve during sterilization.

FIG. 7 is a section view taken along line 7—7 of FIG. 6.

FIG. 8 is a front perspective view of the housing of the apparatus of the present invention illustrating a probe disposed in a sleeve adapted therefor and contact lens disposed in another sleeve adapted therefor.

FIG. 9 is a section view taken along line 9—9 of FIG. 8.

DESCRIPTION OF PREFERRED EMBODIMENTS

Figure 1:
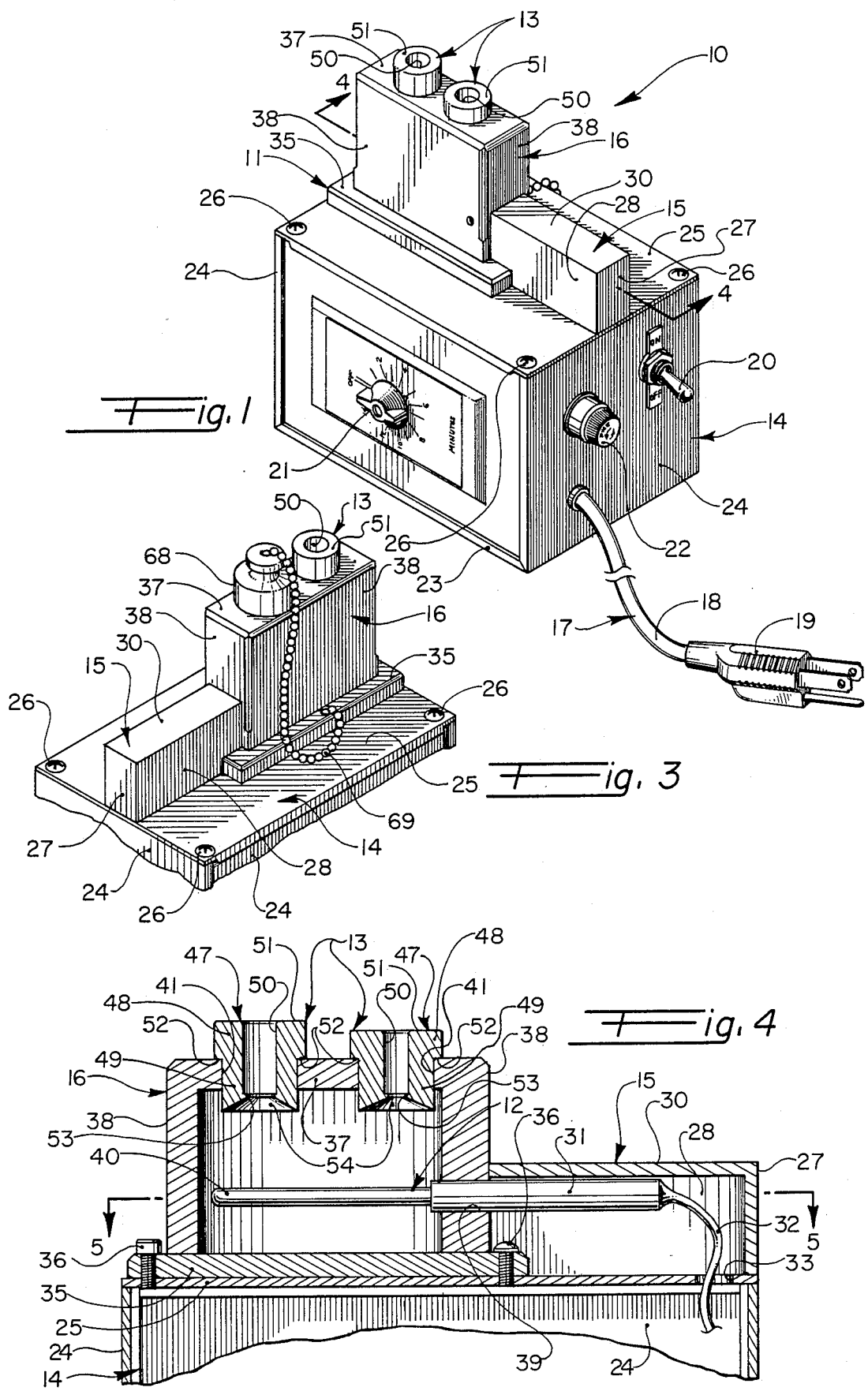
FIG. 1 is a front perspective view of the apparatus of the present invention.
Figure 2:
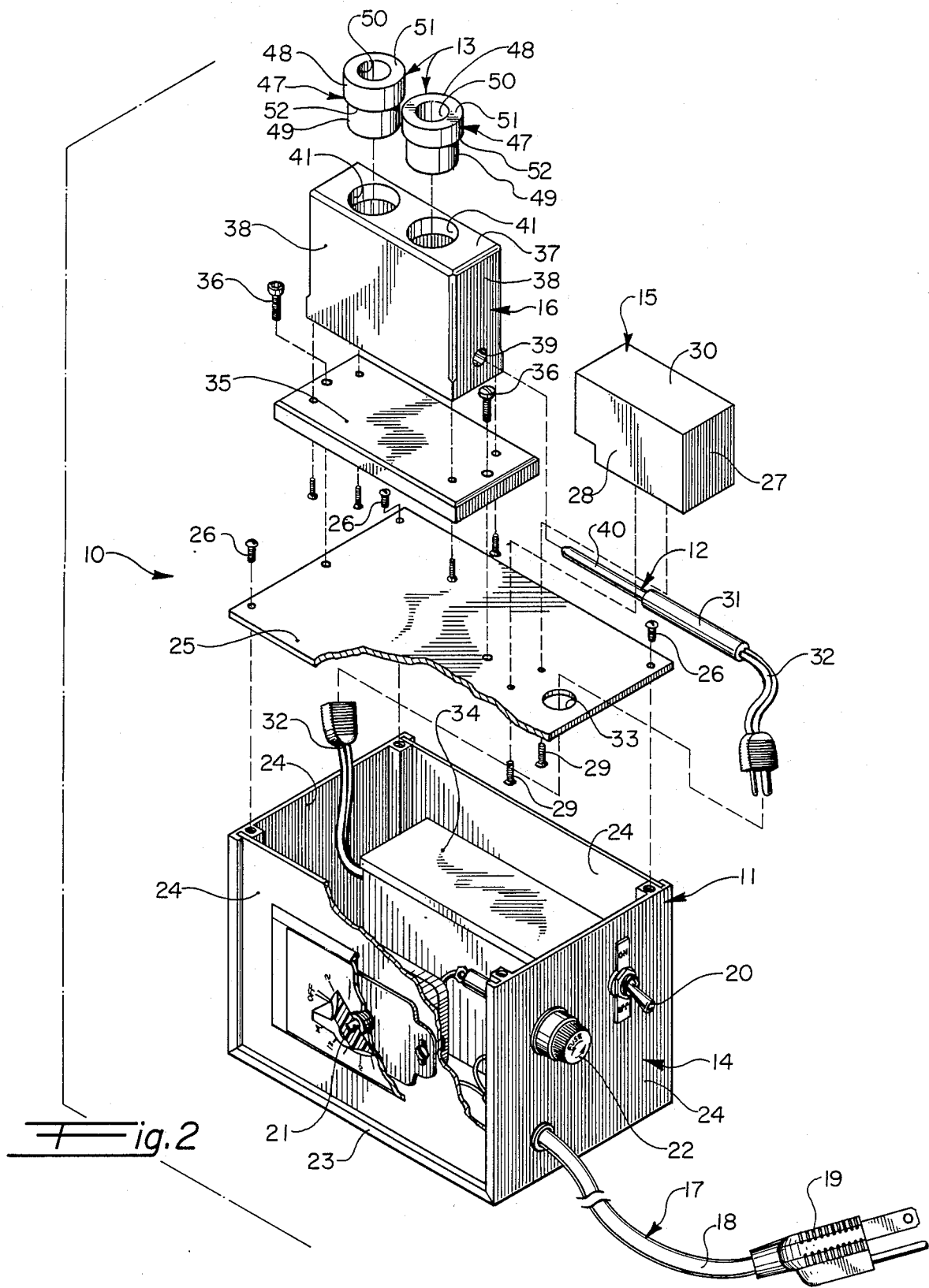
FIG. 2 is an exploded view, in perspective, of the apparatus of the present invention with portions thereof broken away for the sake of clarity.

With reference now to FIGS. 1-5, the apparatus 10 for sterilizing ophthalmological devices and instruments which have a portion thereof intended to be placed into contact with a patient's eye, such as probes and contact lens, is seen to include an enclosed housing 11, an ultraviolet light source 12 positioned within the housing 11 and, preferably, two (and at least one) ophthalmological instrument insert sleeves 13.

Housing 11 includes an electronics (transformer) housing portion 14, an ultraviolet light source housing portion 15 and a sterilization housing portion (insert holder housing) 16. Positioned in the electronics housing portion 14 is a conventional transformer 34 (FIG. 2) and its associated electronics, which are of a variety that are well known to those skilled in the art. A first electrical conduit means 17 in the form of electrical cord 18 and plug 19 is positioned between and in electrical communication with the transformer 34 and an external electrical power source such as a conventional electrical wall outlet, which are also well known to those skilled in the art. In doing so, the electrical cord 18 extends through a wall of the housing portion 14. In this manner, the first electrical conduit means 17 carries electrical power from the external power source to the transformer 34.

An on/off switch means 20 and an on/off timer switch means 21, each of which are conventional and are well known to those skilled in the art, provide for, respectively, selective, manual control of the flow of electrical power between the power source and the transformer 34 and for manually presetting the desired time of sterilization by the ultraviolet light source.

A fuse 22 is also provided to prevent damage to the electronics.

Housing portion 14 includes a base 23. A pair of two parallel vertical side walls 24 are positioned about the perimeter of the base 23. A top wall 25 is positioned parallel to the base 23. The side walls 24 are further positioned about the perimeter of the top wall 25, whereby the housing portion 14 is enclosed. The housing portion, including base 23, side walls 24 and top wall 25, may either be formed as an integral piece or, preferably, the top wall 25 may be removably secured to the side walls 24 by suitable means such as screws 26. This permits access to the transformer 34 and its associated electronics.

Ultraviolet light source housing portion 15 includes a vertical end wall 27 and a pair of parallel vertical side walls 28, each of which have an edge that is integrally formed with an edge of the end wall 27. The end wall 27 and the side walls 28 are each positioned on the top wall 25 of the housing portion 14 and may be either integral therewith, or may be secured thereon by screws 29. In this fashion, the top wall 25 of the housing portion 14 forms a base for the light source housing portion 15. A top wall 30 is positioned on, and is integral with, the side walls 28 and the end wall 27 of the light source housing portion 15.

Positioned within housing portion 15 is the electrical outlet 31 for an ultraviolet light 40. A second electrical conduit means 32 is positioned between the transformer 34 and the electrical outlet 31. In doing so, the conduit means 32 extends through an aperture 33 formed in top wall 25 of the housing 14. The second electrical conduit means 32 is further electrically connected to the electrical outlet 31 and the transformer 34, wherein electrical power is carried from the transformer 34 to the outlet 31.

Sterilization housing portion (insert holder housing) 16 is positioned on the top wall 25 of housing portion 14. Sterilization housing portion 16 has a base 35 which may be either integrally formed with the top wall 25 of housing 14 or which may be secured thereto by screws 36. The housing portion 16 further includes an upper wall 37 and four downwardly-extending side walls 38. Side walls 38 are positioned on the base 35 and are secured thereto in a light tight fit—that is, so that light cannot pass between the base 35 and side walls 18. Secured to one of the sidewalls 38 are the top wall 30 and the side walls 28 of the UV light source housing portion 15. The electrical outlet 31 (part of the light source) is positioned extending through aperture 39 formed in one of the side walls 38, where it is mounted and carried by the side wall 38. Preferably, the interior surface of housing portion 16 is a highly polished concave reflecting surface.

An ultraviolet light bulb 40 is received in the electrical outlet, such that electrical power in the outlet 31 energizes the bulb 40. Preferably, the ultraviolet light source includes an ultraviolet light bulb having a wavelength of 254 NM. It is noted that the bulb 40 is a normal, straight, elongated UV bulb 40. While not limited to such a shape, it is noted that such a configuration is cheaper, more readily available and easier to use and maintain than the convoluted shaped bulbs utilized in the prior art. This forms a substantial advantage over those convoluted bulbs utilized in the prior art.

Together, the transformer 34, the first electrical conduit means 17, the on/off switch means 20, the electrical outlet 31, the timer switch means 21, the fuse 22, the second electrical conduit means 32 and the ultraviolet light bulb 40 comprise the light source.

Formed in the top wall 37 of the insert holder 34, above the UV light 40 which is positioned within the housing 34, is at least one, and preferably two or more, insert sleeve apertures 41. If desired, each insert sleeve aperture 41 may accommodate various different insert sleeves 13 with a relatively close interfit (a snug fit) therebetween. With the exception of the apertures 41, the entire insert holder housing 16 is "light tight", so that light, particularly light from the UV light bulb 40, is prevented from passing therefrom.

With additional reference now to FIGS. 6-9, at least one, and preferably two or more ophthalmological instrument insert sleeves 13 are provided. Each of said sleeves 13 is adapted to removably and snugly receive therein an ophthalmological instrument, such as a probe (i.e., a pneumoprobe or a tonometer probe) or a contact lens, with a relatively close interfit (a snug fit) therebetween. In this manner, light is prevented from passing between both the instrument and the respective sleeve in which it is received. Furthermore, each of said sleeves 13 is removably and snugly received in a respective insertion aperture during use with a relatively close interfit (a snug fit) therebetween, so that light is prevented from passing between the sleeve 13 and the respective aperture 41 in which it is received.

In this manner, during use of the device 10, each of said instruments is held by a respective sleeve 13 below the insert sleeve aperture 41, and into the housing 16, in close proximity to the light source 40.

Figures 10, 11:
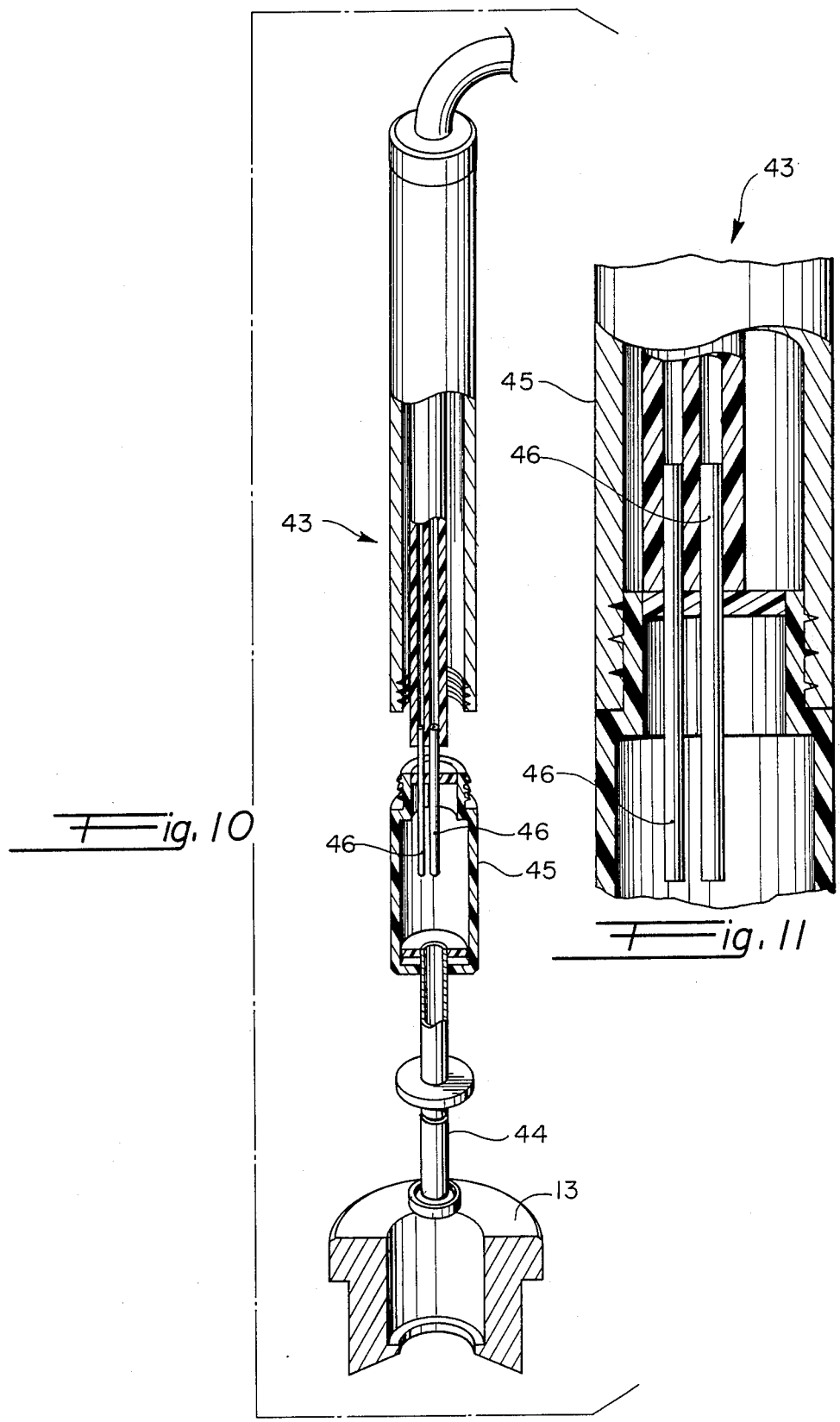
FIG. 10 is an exploded view of an ophthalmological instrument adapted to be received by a sleeve of the present invention.
FIG. 11 is a partial view, to an enlarged scale, of the ophthalmological instrument of FIG. 10 with parts thereof broken away for the sake of clarity.

With reference now to FIGS. 10 and 11, the construction of a probe or meter 43, such as a pneumoprobe or a tonometer probe, which has a portion thereof which contacts the eye of a patient, is illustrated. The probe tip 44, which contacts the eye, is slidably received in a probe body 45. The movement of the probe tip 44 is sensed by measuring rods 46 which electronically transmits the sensed movement to a translator which translates and displays the sensed movement.

Returning now to FIGS. 1-9, each of the insert sleeves 13 includes an insert sleeve body portion 47 which, preferably, is formed having a highly reflective surface. The body portion 47 has an upper end 48 and a lower end 49. The insert sleeve body 47 further has a longitudinal bore 50 formed therethrough, wherein the instrument to be sterilized is received in the sleeve 42. Longitudinal bore 50 is preferably sized having a diameter that, while being slightly larger than the diameter of the probe body 45, nonetheless, provides a relatively tight interfit (a snug fit) between the bore 50 and the probe body 45.

Formed on the upper end 48 of the sleeve body 47 is a boss 51. An external annular shoulder 52 is defined by (between) the boss 51 and the body 47. When at least a portion of the sleeve body 47 is received through its respective aperture 41 and into the housing 16, the annular shoulder 52 abuts the insert holder housing 16, thereby preventing further movement of the sleeve 47 into the insert holder housing 16. In this manner, a means is provided for limiting the extent to which the insert sleeve 47 is received in the housing 16. The boss 51, by being positioned overlying and abutting the top wall 37 aids in preventing UV light from passing between the sleeve body 47 and the aperture 41.

On the lower end 49 of the sleeve body 47, there is formed an internal annular lip 53. When the probe is received in the insert sleeve 13 during use, the probe body 45 abuts the internal annular lip 53, thereby preventing further movement of the probe into the sleeve 13. In this manner, a means is provided for limiting the extent to which the ophthalmological device extends below the insert sleeve 13. Due to gravity, the probe tip 44 will extend fully from the probe body 45 and through the lower end of the bore 50, so that it emerges fully from the lower end 49 of the sleeve 13. This allows the probe tip 44 to be fully exposed to the UV light for the sterilization thereof. This annular lip 53, by overlying and abutting the top of the probe body 45, aids in preventing UV light from the light source from passing between the sleeve 13 and its respective aperture 41.

The lower end 49 of the sleeve body 47 has a countersunk portion 54 formed therein, which terminates coincident with the internal annular lip 53. This countersunk portion 54 aids in reflecting light in the direction of the probe tip 44. In this fashion, areas of the probe tip 44, which due to its construction and shape, would otherwise be shaded from direct light from the UV light 40, are sterilized by UV light reflected by the surface of the countersunk portion 54.

With reference now to FIGS. 8 and 9 the insert sleeve 42, adapted to receive contact lenses therein, includes an insert sleeve body portion 55 having an upper end 56 and a lower end 57. A boss 58 is formed on the upper end 56 of the sleeve body 55. An external annular shoulder 59 is defined between (by) the boss 58 and the sleeve body 55. When the sleeve is received in a respective sleeve aperture 41 during use, the annular shoulder 59 abuts the insert holder housing 16, thereby preventing further movement of the sleeve 42 into the insert holder housing 16. In this manner, a means is provided for limiting the extent to which the insert sleeve 42 is received in the housing 16. The boss 58, by overlying and abutting the top wall 37, also aids in preventing UV light from passing between the sleeve 42 and the aperture 41 in which it is received.

Preferably, this upper portion 56 is formed having a highly reflective surface to reflect UV light for sterilization purposes. A pocket 60 is suspended from, and is carried by, the lower end 57 of the sleeve body 55. This pocket 60 includes a lower shelf 6 having an aperture 62 formed therein. An upwardly-extending annular lip 63 is formed on the lower shelf 61 about the periphery thereof. The pocket 60 is suspended by at least one post member 64. Preferably at least two post members 64 are provided. Each post member 64 has an upper end which is piloted in the lower end of the insert sleeve 42. Each post member 64 further has a lower end which is piloted in the annular lip 63 of the lower shelf 61.

A clear cup member 65 is adapted to be removably received in the pocket 60 being supported therein by the lower shelf 61. This clear cup member 65, which is UV light permeable, is adapted to receive therein the contact lens to be sterilized. This cup member 65 includes a bottom wall having a perimeter. This cup member 65 further includes an upwardly-extending annular lip 66 formed about the perimeter of the bottom wall. This lip 66 aids in preventing the lens from being accidentally dislodged from the sleeve 42.

When received in the pocket 60, the bottom wall of the cup member 65 and the aperture 62 of the lower shelf 61 of the pocket 60 are substantially aligned with one another, so that the contact lens are fully exposed to the UV light.

If desired, a lid member 67 is also provided. This lid member 67 is adapted to fit over the cup member 65. When placed on the cup member, the lid member 67 removably retains the contact lens within the cup member 65.

If only one of a possible plurality of insert sleeves 42 are being used at any time, at least one cap 68 is provided which is sized to be received over the boss 51 of a respective sleeve 42. The cap 68 thereby covers the opening created by the bore 50. In this fashion, light is prevented from passing through each unused sleeve 42. If desired, a chain 69 may be provided having a first end which is secured to each cap 68. The chain 69 further has a second, opposite end which is secured to the housing 11. In this fashion, the chain 69 would be secured to the housing 11, preventing the chain 69, and its respective cap 68, from being accidentally lost.

In use, the apparatus 10 is first readied by placing switch 20 in the off position. A sleeve 13 for each of the ophthalmological instruments to be sterilized is then selected. The selected sleeve should be that sleeve 13 which is adapted to receive therein the particular ophthalmological instrument to be sterilized.

The instrument to be sterilized is then manually slid into its respective longitudinal bore 50, so that the probe body 45 abuts the internal annular lip 53 of the sleeve having the probe tip 44 emerging from the lower end 49 of the sleeve 13.

Each of the sleeves 13 is then slidably, manually disposed in a respective insert holder aperture 41, such that the sleeve 13 has at least a portion thereof received in the housing 16. The extent to which the sleeve 13 is received in the housing 16 is limited by the contact between boss 51 and the top wall 37. A cap 68 is then disposed over the boss 51 of each unused sleeve 13.

The timer switch 21 is then set for the time interval desired for sterilization. The on/off switch 20 is then placed in the "on" position, whereby power from the external outlet is carried to the electrical outlet 31 via the first conduit means 17, transformer 34 and the second conduit means 32, respectively. Power in outlet 31 energizes the UV light bulb 40 which radiates the UV light that sterilizes the probe tip 44. Areas of the probe tip 44 which are shaded and/or otherwise blocked from direct UV light (radiation), are indirectly radiated by light reflected off the interior surface of the housing 16 and/or the countersunk portion 54 of sleeve 13. In the instance where the sleeve 42 is adapted to carry contact lenses, the UV light passes through the aperture of the lower shelf 61 and the clear cup member 65 to sterilize the lens. UV light is also reflected off the interior surface of housing 16 and the lower end 57 of the sleeve 42 to indirectly radiate the shaded areas of the contact lens.

When the desired time of sterilization is completed, the timer switch 21 automatically shuts the device off, so that the sterilized ophthalmological device may be removed therefrom.

Obviously, many modifications may be made without departing from the basic spirit of the present invention. Accordingly, it will be appreciated by those skilled in the art that within the scope of the appended claims, the invention may be practiced other than has been specifically described herein.

What is claimed is:

1. An apparatus for sterilizing ophthalmological instruments, comprised of:
    an enclosed housing having at least one insert sleeve aperture formed therein;
    an ultraviolet light source positioned within the housing;
    at least one ophthalmological instrument insert sleeve, each sleeve removably and snugly receiving therein an ophthalmological instrument, and each of said sleeves being removably and snugly received in a respective insertion aperture during use, so that each said instrument is held by a respective sleeve in close proximity to the light source, and further so that light is prevented from passing between both the instrument and the respective sleeve in which it is received and the sleeve and the respective aperture in which it is received.

2. An apparatus for sterilizing ophthalmological instruments, comprised of:
    an enclosed insert holder including a housing having a highly polished reflecting interior surface, said housing further having at least two insert sleeve apertures formed therein;
    an ultraviolet light source positioned within the housing;
    at least two ophthalmological instrument insert sleeves, each of said sleeves having a close tolerance with a respective ophthalmological instrument, so as to selectively, removably and snugly receive therein the respective ophthalmological instrument, so that during use, light is prevented from passing between the sleeve and the respective instrument received therein, each of said sleeves further having a close tolerance with a respective insertion sleeve aperture, so as to be selectively, removably and snugly received in the insert sleeve aperture, so that during use, light is prevented from passing between the sleeve and the respective insert sleeve aperture in which the sleeve is received; and
    wherein, during use each of said instruments is held by a respective sleeve in close proximity to the light source.

3. The apparatus of claim 2, further including at least one cap, each of said caps sized to be received over a respective sleeve, whereby light is prevented from passing through the sleeve.

4. The apparatus of claim 2, wherein the light source is comprised of:
    a transformer;
    a first electrical conduit means positioned between and in electrical communication with the transformer and an external electrical power source, wherein electrical power from the external electrical power source is carried to the transformer;
    an on/off switch means for selectively, manually controlling the flow of electrical power between the power source and the transformer;
    an electrical outlet for an ultraviolet light;
    a second electrical conduit means positioned between, and in electrical communication with the transformer and the electrical outlet, wherein electrical power is carried from the transformer to the outlet; and
    an ultraviolet light bulb received in the electrical outlet, such that electrical power in the outlet energizes said bulb.

5. The apparatus of claim 4, wherein the transformer, the on/off switch and the second electrical conduit means are positioned in a transformer housing, and further wherein the electrical outlet is disposed through the housing of the insert holder.

6. The apparatus of claim 4, further including an adjustable on/off timer switch means for manually presetting the desired time of sterilization by the ultraviolet light source.

7. The apparatus of claim 2, wherein the housing of the insert holder includes an upper wall and four downwardly-extending sidewalls, the upper wall having the insert sleeve apertures formed therein and the light source being mounted on one of the sidewalls, such that during use the sleeves are received in a respective aperture positioned directly over the light source and in close proximity thereto.

8. The apparatus of claim 2, wherein the ultraviolet light source is an ultraviolet light having a wavelength of 254 NM.

9. The apparatus of claim 2, wherein each insert sleeve aperture may accommodate various different insert sleeves adapted to accommodate various ophthalmological instruments including test probes and contact lenses.

10. The apparatus of claim 2, wherein at least one insert sleeve may receive therein a pneumoprobe.

11. The apparatus of claim 10, wherein each insert sleeve receiving the pneumoprobe having a probe body and a probe tip, is comprised of:
    an insert sleeve body portion having an upper end, and a lower end, the insert sleeve body further having a longitudinal bore formed therethrough, wherein the pneumoprobe to be sterilized is received in the sleeve;
    a boss formed on the upper end of the sleeve body, wherein an external annular shoulder is defined between the boss and the sleeve body and further wherein when the sleeve is received in a respective insert sleeve aperture during use, the annular shoulder abuts the insert holder housing, thereby preventing further movement of the sleeve into the insert holder housing;
    an internal annular lip formed in the bore on the lower end of the sleeve body, wherein when the probe is received in the insert sleeve during use, the probe body abuts the internal annular lip, thereby preventing further movement of the probe into the insert sleeve;
    the lower end of the sleeve body having a countersunk portion formed therein, the countersunk portion terminating coincident with the internal annular lip; and wherein when the probe is received in the respective sleeve during use, the probe tip thereof emerges from the lower end of the sleeve, so that the probe tip is exposed to the ultraviolet light.

12. The apparatus of claim 2, wherein at least one insert sleeve may receive therein a tonometer probe.

13. The apparatus of claim 12, wherein each insert sleeve receiving the tonometer having a probe body and a probe tip, is comprised of:
an insert sleeve body portion having an upper end and a lower end, the insert sleeve body further having a longitudinal bore formed therethrough, wherein the tonometer probe to be sterilized is received in the sleeve;
a boss formed on the upper end of the sleeve body, wherein an external annular shoulder is defined between the boss and the sleeve body, and further wherein when the sleeve is received in a respective insert sleeve aperture during use, the annular shoulder abuts the insert holder housing, thereby preventing further movement of the sleeve into the insert holder housing;
an internal annular lip formed in the bore on the lower end of the sleeve body, wherein when the probe is received in the insert sleeve during use, the probe body abuts the internal annular lip, thereby preventing further movement of the tonometer probe into the insert sleeve;
the lower end of the sleeve body having a countersunk portion formed therein, the countersunk portion terminating coincident with the internal annular lip; and
wherein when the tonometer probe is received in the respective sleeve during use, the probe tip thereof emerges from the lower end of the sleeve, so that the probe tip is exposed to the ultraviolet light.

14. The apparatus of claim 2, wherein at least one insert sleeve may receive contact lenses therein.

15. The apparatus of claim 14, wherein each insert sleeve receiving contact lenses, is comprised of:
an insert sleeve body portion having an upper end and a lower end;
a boss formed on the upper end of the sleeve body, wherein an external annular shoulder is defined between the boss and the sleeve body, and further wherein when the sleeve is received in a respective insert sleeve aperture during use, the annular shoulder abuts the insert holder housing, thereby preventing further movement of the sleeve into the insert holder housing;
a pocket suspended from and carried by the lower end of the sleeve, said pocket including a lower shelf having an aperture formed therein and an upwardly extending annular lip formed on the lower shelf; and
a clear cup member including a bottom wall having a perimeter and further including an upwardly-extending annular lip formed about the perimeter of the bottom wall, the cup member adapted to receive therein contact lenses to be sterilized, said cup member further adapted to be removably received in the pocket with the bottom wall of the cup member and the aperture of the lower shelf of the pocket substantially aligned with one another, so that the contact lenses are exposed to the ultraviolet light.

16. The apparatus of claim 15, wherein each insert sleeve receiving contact lenses is further comprised of:
a lid member removably received on the upwardly-extending annular lip of the cup member, whereby the contact lenses are removably retained within the cup member.

17. The apparatus of claim 15, wherein each insert sleeve receiving contact lenses is further comprised of:
at least one post member having an upper end being piloted in the lower end of the insert sleeve, and each post member further having a lower end being piloted in the upwardly extending annular lip of the pocket, whereby the pocket is suspended from and carried by the lower end of the sleeve.

18. The apparatus of claim 14, wherein each insert sleeve receiving contact lenses, is comprised of:
an insert sleeve body portion having an upper end and a lower end;
a boss formed on the upper end of the sleeve body, wherein an external annular shoulder is defined between the boss and the sleeve body, and further wherein when the sleeve is received in a respective insert sleeve aperture during use, the annular shoulder abuts the insert holder housing, thereby preventing further movement of the sleeve into the insert holder housing;
a pocket including a lower shelf having an aperture formed therein and an upwardly extending annular lip formed on the lower shelf;
at least one post member having an upper end being piloted in the lower end of the insert sleeve, and each post member further having a lower end being piloted in the upwardly extending annular lip of the pocket, whereby the pocket is suspended from and carried by the lower end of the sleeve;
a clear cup member including a bottom wall having a perimeter and further including an upwardly-extending annular lip formed about the perimeter of the bottom wall, the cup member receiving therein contact lenses to be sterilized, said cup member further removably received in the pocket with the bottom wall of the cup member and the aperture of the lower shelf of the pocket substantially aligned with one another, so that the contact lenses are exposed to the ultraviolet light; and
a lid member removably received on the upwardly-extending annular lip of the cup member, whereby the contact lenses are removably retained within the cup member.

19. An apparatus for sterilizing ophthalmological instruments, comprised of:
an enclosed insert holder including a housing having a highly polished reflecting interior surface, said housing further having at least two insert sleeve apertures formed therein;
an ultraviolet light source positioned within the housing including;
a transformer;
a first electrical conduit means positioned between and in electrical communication with the transformer and an external electrical power source, wherein electrical power from the external electrical power source is carried to the transformer;
an on/off switch means for selectively, manually controlling the flow of electrical power between the power source and the transformer;
an electrical outlet for an ultraviolet light;
a second electrical conduit means positioned between and in electrical communication with the transformer and the electrical outlet, wherein electrical power is carried from the transformer to the outlet;

an ultraviolet light bulb having a wavelength of 254 NM, said bulb being received in the electrical outlet, such that electrical power in the outlet energizes said bulb;

at least two ophthalmological instrument insert sleeves, each of said sleeves having a close tolerance with a respective ophthalmological instrument, so as to selectively, removably and snugly receive therein the respective ophthalmological instrument, so that during use light is prevented from passing between the sleeve and the respective instrument received therein, each of said sleeves further having a close tolerance with a respective insertion sleeve aperture, so as to be selectively, removably and snugly received in the insert sleeve aperture, so that during use light is prevented from passing between the sleeve and the respective insert sleeve aperture in which the sleeve is received;

wherein the housing of the insert holder includes an upper wall and four downwardly-extending sidewalls, the upper wall having the insert sleeve apertures formed therein and the light source being mounted on one of the sidewalls, such that during use the sleeves are received in a respective aperture positioned directly over the light source and in close proximity thereto;

further including at least one cap, each of said caps sized to be received over a respective sleeve, whereby light is prevented from passing through the sleeve;

wherein the transformer, the on/off switch and the second electrical conduit means are positioned in a transformer housing and further wherein the electrical outlet is disposed through the housing of the insert holder;

further including an adjustable on/off timer switch means for manually presetting the desired time of sterilization by the ultraviolet light source.

20. An apparatus for sterilizing ophthalmological instruments including pneumoprobes, tonometer probes and contact lenses, comprised of:

an enclosed insert holder including a housing having a highly polished reflecting interior surface, said housing further having at least two insert sleeve apertures formed therein;

an ultraviolet light source positioned within the housing including;

a transformer;

a first electrical conduit means positioned between and in electrical communication with the transformer and an external electrical power source, wherein electrical power from the external electrical power source is carried to the transformer;

an on/off switch means for selectively, manually controlling the flow of electrical power between the power source and the transformer;

an electrical outlet for an ultraviolet light;

a second electrical conduit means positioned between and in electrical communication with the transformer and the electrical outlet, wherein electrical power is carried from the transformer to the outlet;

an ultraviolet light bulb received in the electrical outlet, such that electrical power in the outlet energizes said bulb;

a plurality of ophthalmological instrument insert sleeves, each of said sleeves having a close tolerance with a respective ophthalmological instrument, so as to selectively, removably and snugly receive therein the respective ophthalmological instrument, so that during use light is prevented from passing between the sleeve and the respective instrument received therein, each of said sleeves further having a close tolerance with a respective insertion sleeve aperture, so as to be selectively, removably and snugly received in the insert sleeve aperture, so that during use light is prevented from passing between the sleeve and the respective insert sleeve aperture in which the sleeve is received; and wherein each insert sleeve aperture may accommodate various different insert sleeves to accommodate various ophthalmological instruments including test probes and contact lenses;

at least one insert sleeve receiving therein a pneumoprobe having a probe body and a probe tip, said insert sleeve including an insert sleeve body portion having an upper end, and a lower end, the insert sleeve body further having a longitudinal bore formed therethrough, wherein the pneumoprobe to be sterilized is received in the sleeve; a boss formed on the upper end of the sleeve body, wherein an external annular shoulder is defined between the boss and the sleeve body and further wherein when the sleeve is received in a respective insert sleeve aperture during use, the annular shoulder abuts the insert holder housing, thereby preventing further movement of the sleeve into the insert holder housing; an internal annular lip formed in the bore on the lower end of the sleeve body, wherein when the probe is received in the insert sleeve during use, the probe body abuts the internal annular lip, thereby preventing further movement of the probe into the insert sleeve;

the lower end of the sleeve body having a countersunk portion formed therein, the countersunk portion terminating coincident with the internal annular lip; and wherein when the probe is received in the respective sleeve during use, the probe tip thereof emerges from the lower end of the sleeve, so that the probe tip is exposed to the ultraviolet light;

at least one insert sleeve receiving therein a tonometer probe having a probe body and a probe tip, said insert sleeve including an insert sleeve body portion having an upper end and a lower end, the insert sleeve body further having a longitudinal bore formed therethrough, wherein the tonometer probe to be sterilized is received in the sleeve; a boss formed on the upper end of the sleeve body, wherein an external annular shoulder is defined between the boss and the sleeve body, and further wherein when the sleeve is received in a respective insert sleeve aperture during use, the annular shoulder abuts the insert holder housing, thereby preventing further movement of the sleeve into the insert holder housing;

an internal annular lip formed in the bore on the lower end of the sleeve body, wherein when the probe is received in the insert sleeve during use, the probe body abuts the internal annular lip, thereby preventing further movement of the tonometer probe into the insert sleeve; the lower end of the sleeve body having a countersunk portion formed therein, the countersunk portion terminating coincident with the internal annular lip; wherein when the tonometer probe is received in the respective sleeve during use, the probe tip thereof emerges from the lower end of the sleeve, so that the probe tip is exposed to the ultraviolet light;

at least one insert sleeve receiving therein contact lenses, said insert sleeve including an insert sleeve body portion having an upper end and a lower end;

a boss formed on the upper end of the sleeve body, wherein an external annular shoulder is defined between the boss and the sleeve body, and further wherein when the sleeve is received in a respective insert sleeve aperture during use, the annular shoulder abuts the insert holder housing, thereby preventing further movement of the sleeve into the insert holder housing;

a pocket including a lower shelf having an aperture formed therein and an upwardly extending annular lip formed on the lower shelf;

at least one post member having an upper end being piloted in the lower end of the insert sleeve, and each post member further having a lower end being piloted in the upwardly extending annular lip of the pocket, whereby the pocket is suspended from and carried by the lower end of the sleeve;

a clear cup member including a bottom wall having a perimeter and further including an upwardly-extending annular lip formed about the perimeter of the bottom wall, the cup member receiving therein contact lenses to be sterilized, said cup member further removably received in the pocket with the bottom wall of the cup member and the aperture of the lower shelf of the pocket substantially aligned with one another, so that the contact lenses are exposed to the ultraviolet light; and a lid member removably received on the upwardly-extending annular lip of the cup member, whereby the contact lenses are removably retained within the cup member;

wherein the housing of the insert holder includes an upper wall and four downwardly-extending sidewalls, the upper wall having the insert sleeve apertures formed therein and the light source being mounted on one of the sidewalls, such that during use the sleeves are received in a respective aperture positioned directly over the light source and in close proximity thereto;

further including at least one cap, each of said caps sized to be received over a respective sleeve, whereby light is prevented from passing through the sleeve;

wherein the transformer, the on/off switch and the second electrical conduit means are positioned in a transformer housing and further wherein the electrical outlet is disposed through the housing of the insert holder; and further including an adjustable on/off timer switch means for manually presetting the desired time of sterilization by the ultraviolet light source.

21. An apparatus for sterilizing ophthalmological instruments comprising:

a housing having at least one insert sleeve aperture formed therein;

an ultraviolet light source positioned within the housing;

an insert sleeve received in the insert sleeve aperture; the insert sleeve receiving therein a pneumoprobe having a probe body and a probe tip, said sleeve comprised of:

an insert sleeve body portion having an upper end, and a lower end, the insert sleeve body further having a longitudinal bore formed therethrough, wherein the pneumoprobe to be sterilized is received in the sleeve;

a boss formed on the upper end of the sleeve body, wherein an external annular shoulder is defined between the boss and the sleeve body;

an internal annular lip formed in the bore on the lower end of the sleeve body, wherein when the probe is received in the insert sleeve during use, the probe body abuts the internal annular lip, thereby preventing further movement of the probe into the insert sleeve;

the lower end of the sleeve body having a countersunk portion formed therein, the countersunk portion terminating coincident with the internal annular lip; and wherein when the probe is received in the respective sleeve during use, the probe tip thereof emerges from the lower end of the sleeve, so that the probe tip is exposed to the ultraviolet light.

22. An apparatus for sterilizing ophthalmological instruments comprising:

a housing having at least one insert sleeve aperture formed therein;

an ultraviolet light source positioned within the housing;

an insert sleeve received in the insert sleeve aperture; the insert sleeve receiving therein a tonometer probe having a probe body and a probe tip, said sleeve comprised of:

an insert sleeve body portion having an upper end and a lower end, the insert body further having a longitudinal bore formed therethrough, wherein the tonometer probe to be sterilized is received in the sleeve;

a boss formed on the upper end of the sleeve body, wherein an external annular shoulder is defined between the boss and the sleeve body, and an internal annular lip formed in the bore on the lower end of the sleeve body, wherein when the probe is received in the insert sleeve during use, the probe body abuts the internal annular lip, thereby preventing further movement of the tonometer probe into the insert sleeve;

the lower end of the sleeve body having a countersunk portion formed therein, the countersunk portion terminating coincident with the internal annular lip; and wherein when the tonometer probe is received in the respective sleeve during use, the probe tip thereof emerges from the lower end of the sleeve, so that the probe tip is exposed to the ultraviolet light.

23. An apparatus for sterilizing ophthalmological instruments comprising:

a housing having at least one insert sleeve aperture formed therein;

an ultraviolet light source positioned within the housing;

an insert sleeve received in the insert sleeve aperture, the insert sleeve receiving contact lenses therein, said sleeve comprised of:

an insert sleeve body position having an upper end and a lower end;

a boss formed on the upper end of the sleeve body, wherein an external annular shoulder is defined between the boss and the sleeve body, and further wherein when the sleeve is received in a respective insert sleeve aperture during use, the annular shoulder abuts the insert holder housing, thereby preventing further movement of the sleeve into the insert holder housing;

a pocket including a lower shelf having an aperture formed therein and an upwardly extending annular lip formed on the lower shelf;

at least one post member having an upper end being piloted in the lower end of the insert sleeve, and each post member further having a lower end being piloted in the upwardly extending annular lip of the pocket, whereby the pocket is suspended from and carried by the lower end of the sleeve;

a clear cup member including a bottom wall having a perimeter and further includng an upwardly-extending annular lip formed about the perimeter of the bottom wall, the cup member receiving therein contact lenses to be sterilized, said cup member further being removably received in the pocket with the bottom wall of the cup member and the aperture of the lower shelf of the pocket substantially aligned with one another, so that the contact lenses are exposed to the ultraviolet light; and a lid member removably received on the upwardly-extending annular lip of the cup member, whereby the contact lenses are removably retained within the cup member.

* * * * *